(12) United States Patent
McGlamery, Jr. et al.

(10) Patent No.: US 7,989,669 B2
(45) Date of Patent: Aug. 2, 2011

(54) RECYCLE OF DME IN AN OXYGENATE-TO-OLEFIN REACTION SYSTEM

(75) Inventors: Gerald G. McGlamery, Jr., Houston, TX (US); James H. Beech, Jr., Kingwood, TX (US); Michael P. Nicoletti, Houston, TX (US); Cornelis F. Van Egmond, Pasadena, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 381 days.

(21) Appl. No.: 12/034,425

(22) Filed: Feb. 20, 2008

(65) Prior Publication Data

US 2008/0242908 A1    Oct. 2, 2008

Related U.S. Application Data

(60) Provisional application No. 60/920,428, filed on Mar. 28, 2007.

(51) Int. Cl.
*C07C 2/02* (2006.01)
(52) U.S. Cl. ........ 585/518; 585/520; 585/638; 585/639; 585/640; 585/800; 585/804; 585/809
(58) Field of Classification Search .................. 585/518, 585/520, 638, 639, 640, 800, 804, 809
See application file for complete search history.

(56) References Cited

U.S. PATENT DOCUMENTS

| | | | |
|---|---|---|---|
| 6,844,480 B2 | 1/2005 | Lattner et al. | |
| 6,855,858 B2 | 2/2005 | Cheng et al. | |
| 7,005,555 B2 | 2/2006 | Ding et al. | |
| 7,060,866 B2 | 6/2006 | Van Egmond et al. | |
| 7,067,597 B2 | 6/2006 | Van Egmond et al. | |
| 7,070,491 B2 | 7/2006 | Becksvoort | |
| 7,074,971 B2 | 7/2006 | Van Egmond et al. | |
| 7,214,846 B2 | 5/2007 | Van Egmond et al. | |
| 7,238,848 B2 | 7/2007 | Borgmann et al. | |
| 2003/0004386 A1* | 1/2003 | Lattner et al. ................ 585/804 |
| 2003/0125597 A1 | 7/2003 | Cheng et al. | |
| 2003/0199721 A1 | 10/2003 | Ding et al. | |
| 2004/0064009 A1 | 4/2004 | Borgmann et al. | |
| 2006/0111601 A1 | 5/2006 | Cheng et al. | |

FOREIGN PATENT DOCUMENTS

WO    WO03/020678    3/2003

* cited by examiner

*Primary Examiner* — Prem C Singh
(74) *Attorney, Agent, or Firm* — Kevin M. Faulkner; David M. Weisberg

(57) ABSTRACT

This invention is directed to a process for producing one or more olefins from an oxygenate feed. According to the invention, an oxygenate stream is provided and a recycle stream is added to the oxygenate stream to form a feed stream to an oxygenate-to-olefin conversion system. The recycle stream comprises (i.e., contains) propane and dimethyl ether.

17 Claims, 2 Drawing Sheets

RECYCLE OF DME IN AN OXYGENATE-TO-OLEFIN REACTION SYSTEM

CROSS-REFERENCE TO RELATED APPLICATIONS

This application claims priority to and the benefit of U.S. Provisional Application Ser. No. 60/920,428, filed Mar. 28, 2007.

FIELD OF THE INVENTION

This invention relates to the production of olefins, in particular light olefins such as ethylene and propylene, from oxygenates. In particular, this invention relates to the production of light olefins from an oxygenate feed to which a recycle steam containing dimethyl ether and propane has been added.

BACKGROUND OF THE INVENTION

Olefins, particularly ethylene and propylene, are desirable as a feed source for making derivative products such as oligomers, e.g., higher olefins, and polymers such as polyethylene and polypropylene. Olefin feed sources have traditionally been produced by cracking petroleum feedstocks.

Oxygenate feedstocks, however, are becoming an alternative to petroleum feedstocks for making olefins, particularly large quantities of ethylene and propylene, for the production of higher olefins and plastic materials. In general, the olefins are formed by contacting the oxygenate components, such as methanol, with a molecular sieve catalyst to catalytically convert the oxygenates to olefins. These types of processes are generally referred to as oxygenate-to-olefins (OTO) and methanol-to-olefins (MTO) processes.

Various byproducts are also produced in the OTO and MTO processes. An example of one such byproduct is propane. Propane is extremely difficult to separate from dimethyl ether (DME), which can also be present as a byproduct or as an unreacted feed component. Conventional methods for removing or separating propane from DME involve various extraction or distillation-type processes.

DME that has been separated from the propane byproduct and recovered from the OTO or MTO process can be recycled to the feed going to the reactor. For example, U.S. Pat. No. 6,844,480 (Lattner et al.) discloses removing dimethyl ether from an olefin stream by first separating the olefin stream into a first stream comprising dimethyl ether and lighter boiling point compounds and a second stream comprising $C_{4+}$ olefins and higher boiling point hydrocarbons. The dimethyl ether is then separated from the first stream using extractive distillation. When methanol is used as the extractant, the methanol and dimethyl ether can be combined with the feed in an oxygenate-to-olefins reaction system.

U.S. Pat. No. 6,855,858 (Cheng et al.) discloses a method of removing dimethyl ether from an olefin stream. The method includes distilling the olefin stream so that the dimethyl ether is separated out of the olefin stream with the propane. The olefin stream can then be further distilled to provide a polymer-grade ethylene stream and a polymer-grade propylene stream, with each stream containing not greater than about 10 wppm dimethyl ether. The dimethyl ether can be separated from the propane using a water wash. Following the water wash, the dimethyl ether is recovered by vaporization and recycled with the feed to an oxygenate-to-olefins reaction system.

U.S. Pat. No. 7,005,555 (Ding et al.) discloses a process for producing olefins from oxygenates. The process removes oxygenates including carbon dioxide in the bottoms of the quench stream and recycles the oxygenates back to the reactor. Carbon dioxide is removed from the quench bottoms before returning oxygenates in the quench bottoms stream to the reactor.

U.S. Pat. No. 7,060,866 (Van Egmond et al) discloses a method of removing dimethyl ether from an ethylene and/or propylene containing stream. Dimethyl ether is removed at a high pressure, preferably in a distillation column. The high pressure separation has the benefit of providing a relatively low bottoms temperature separation, while allowing for recovery of a highly concentrated ethylene and/or propylene stream.

U.S. Patent Publication No. 2004/0064009 discloses a method for processing an olefin-containing product stream that contains dimethyl ether as a byproduct, with an example of such a product stream arising in the synthesis of olefin from methanol. For separation of the dimethyl ether from the product stream, it is proposed that at least a partial stream chiefly containing $C_3$ hydrocarbons is separated from the product stream by fractionation, and is sent to a rectification column ($C_3$ splitter) for separation of propylene and propane. The dimethyl ether goes together with the propane into the bottom of the rectification column in the rectification process and can be withdrawn. A substantially pure propylene product, which contains at most only traces of dimethyl ether, can be removed from the top of the rectification column.

U.S. Patent Publication No. 2005/0033103 discloses processes and systems for separating polymerization-grade ethylene and propylene from an initial effluent stream comprising ethane, ethylene, propylene, dimethyl ether, and one or more of propane, acetylene, methyl acetylene, propadiene, methane, hydrogen, carbon monoxide, carbon dioxide and $C_{4+}$ components. In one embodiment, the initial effluent stream is provided from a methanol-to-olefin reaction system. Efficient separation of these components is said to be realized when DME is partially removed in a first separation step comprising methanol and water washing steps, followed by separation of the remaining components in additional separation steps.

A problem is that DME recovery processes are generally quite complex, and there can be significant DME in the propane byproduct stream such that the DME is typically too valuable to discard or use as fuel as would be done with the propane. It is, therefore, desirable to find more efficient ways to recover and/or recycle DME for recycle as feed in the MTO process.

SUMMARY OF THE INVENTION

This invention provides a relatively simple approach to recovering significant quantities of DME and using the DME for recycle as feed in the MTO process. This invention is largely accomplished by recycling propane along with the DME back to the MTO process.

According to one aspect of the invention, there is provided a process for producing one or more olefins from an oxygenate feed. The process includes providing an oxygenate stream and adding a recycle stream containing propane and dimethyl ether to the oxygenate stream to form a feed stream. The feed stream is contacted with an oxygenate-to-olefin catalyst in a reactor to form an olefin stream that contains dimethyl ether, at least one olefin, and propane, with the propane in the olefin stream being in excess of that in the feed stream.

In one embodiment of the invention, at least a majority of the propane and dimethyl ether is separated from the olefin stream to form a propane/DME-containing stream. Preferably, a portion of the propane is removed from the propane/DME-containing stream to form the recycle stream. More preferably, wherein the propane that is removed is in an amount at least equal to the excess.

In one embodiment, the propane is removed by purge or distillation. In another embodiment, the propane is removed by distillation.

In another preferred embodiment, the propane is removed as a side draw in a distillation unit. Preferably, the propane is removed as a side draw from a lower portion of a distillation column.

In yet another embodiment the recycle stream contains from 0.5 wt % to 50 wt % propane, based on total weight of the recycle stream. In still another, the recycle stream contains from 50 wt % to 99 wt % dimethyl ether, based on total weight of the recycle stream.

According to another aspect of the invention, the feed stream is contacted with an oxygenate-to-olefin catalyst in a reactor to form an olefin stream that contains water, dimethyl ether, at least one olefin, and propane, with the propane in the olefin stream is in excess of that in the feed stream. Preferably, water is condensed from the olefin stream to form a liquid stream and a vapor stream. The vapor stream comprises at least a majority of the dimethyl ether, a majority of the at least one olefin and a majority of the propane from the olefin stream. At least a majority of the propane and dimethyl ether present in the olefin stream is separated to form a propane/DME-containing stream; and a portion of the propane is removed from the propane/DME-containing stream to form the recycle stream. Preferably, propane is removed from the propane/DME-containing stream in an amount that is at least equal to the excess so as to form the recycle stream.

According to another aspect of the invention, the olefin stream can be contacted with a polymerization catalyst to form a polymer product.

BRIEF DESCRIPTION OF THE DRAWINGS

Various embodiments of the overall invention are shown by way of example in the attached Figures, wherein.

DETAILED DESCRIPTION OF THE INVENTION

Figure 1:
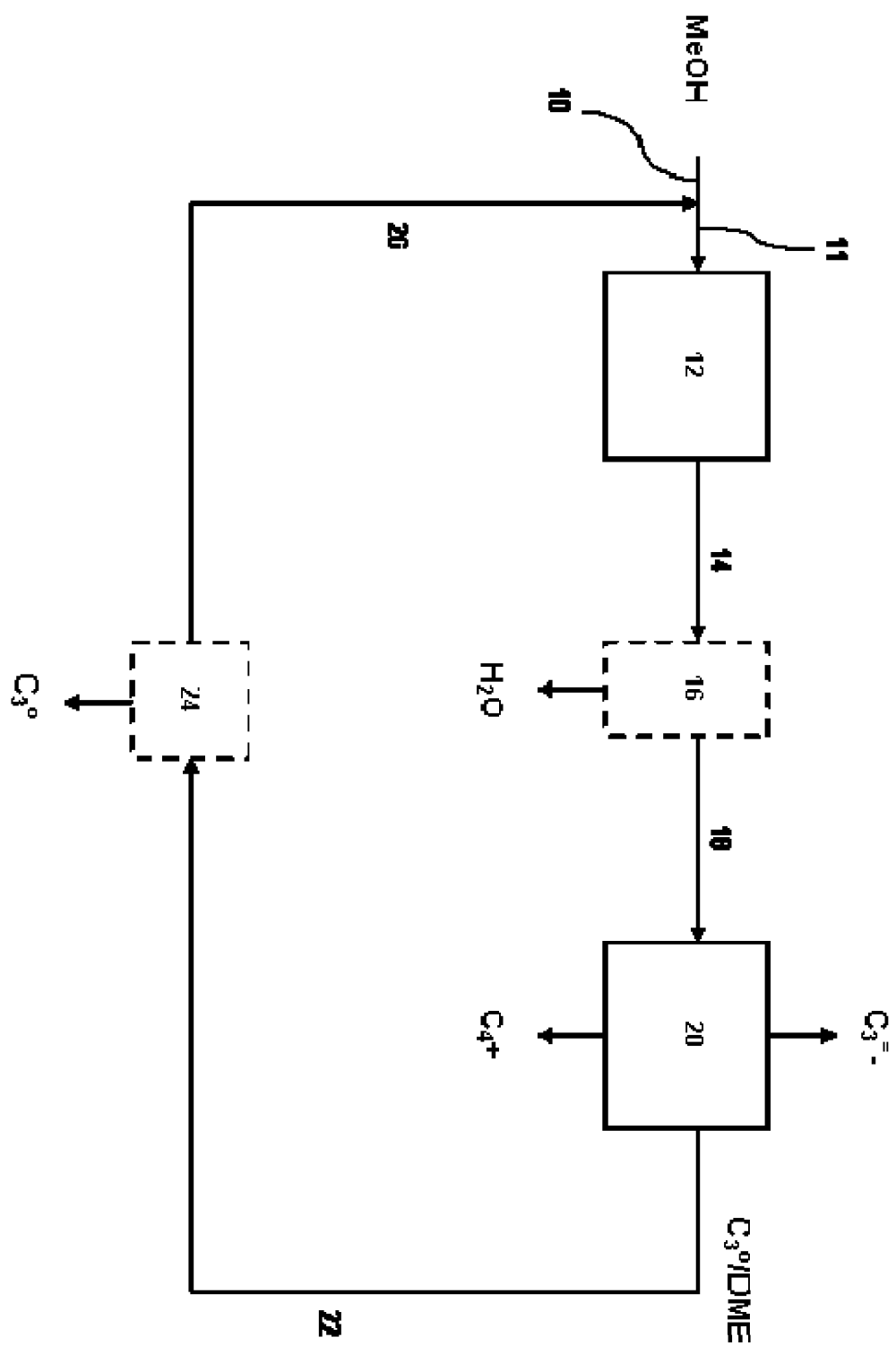
FIG. 1 is a flow diagram of one embodiment of the invention in which a stream containing dimethyl ether and propane is separated and recycled to an oxygenate-to-olefins reaction system.

I. Recycling Dimethyl Ether for Additional Feed

This invention enables a substantial amount of dimethyl ether (DME) to be recycled and used as a feed component in an oxygenate-to-olefins conversion process. The invention is relatively simple in nature in that the DME is recycled in combination with a portion of the propane that is produced in the oxygenate-to-olefin process. Although the propane will be inert in the oxygenate-to-olefin reaction, it can nevertheless be passed back through the reactor as long as propane is removed from the recycle loop in an amount that is at least as much as the amount produced in the reactor during the reaction process. This amount of propane produced in the reactor is generally referred to as excess propane. That is, the excess amount is the amount that is in excess of that in the feed stream to the reactor.

According to the invention, an oxygenate stream is provided and a recycle stream is added to the oxygenate stream to form a feed stream to an oxygenate-to-olefin conversion system. The recycle stream comprises (i.e., contains) propane and dimethyl ether. The dimethyl ether can be effectively reacted with an oxygenate conversion catalyst to form olefin product, particularly light olefin product such as ethylene and propylene. The propane is essentially unreactive in the conversion process, but as long as the amount of propane in the recycle and feed is effectively controlled, the conversion to light olefins can be maintained at a relatively high selectivity, without adversely affecting the process. This recycle of propane along with the dimethyl ether can be accomplished without having to significantly change reactor design or capacity.

II. Oxygenate-to-Olefin Reaction Process

In this invention, an oxygenate stream is combined with a recycle stream to form a feed stream, and the feed stream is contacted with the olefin-forming catalyst to form the olefin product. The oxygenate includes one or more organic compound(s) containing at least one oxygen atom. Preferably, the oxygenate includes one or more alcohol(s), preferably aliphatic alcohol(s) where the aliphatic moiety of the alcohol(s) has from 1 to 4 carbon atoms, preferably from 1 to 3 carbon atoms, and most preferably from 1 to 2 carbon atoms.

Non-limiting examples of specific types of oxygenates useful in the invention include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In a preferred embodiment, the feed also includes, in addition to dimethyl ether from the recycle, at least one oxygenate selected from the group consisting of methanol and ethanol; more preferably methanol.

In one embodiment of the invention, an olefin stream is obtained by contacting oxygenate with a molecular sieve catalyst. The oxygenate comprises at least one organic compound which contains at least one oxygen atom, such as aliphatic alcohols, ethers, carbonyl compounds (aldehydes, ketones, carboxylic acids, carbonates, esters, and the like). When the oxygenate is an alcohol, the alcohol includes an aliphatic moiety having from 1 to 10 carbon atoms, more preferably from 1 to 4 carbon atoms. Representative alcohols include but are not necessarily limited to lower straight- and branched-chain aliphatic alcohols and their unsaturated counterparts. Examples of suitable oxygenate compounds include, but are not limited to: methanol; ethanol; n-propanol; isopropanol; $C_4$-$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof.

Molecular sieves capable of converting an oxygenate to an olefin compound include zeolites as well as non-zeolites, and are of the large-, medium-, or small-pore type. Small-pore molecular sieves are preferred in one embodiment of this invention, however. As defined herein, small-pore molecular sieves have a pore size of less than about 5.0 angstroms. Generally, suitable catalysts have a pore size ranging from about 3.5 to about 5.0 angstroms, preferably from about 4.0 to about 5.0 angstroms, and most preferably from about 4.3 to about 5.0 angstroms.

Zeolite materials, both natural and synthetic, have been demonstrated to have catalytic properties for various types of hydrocarbon conversion processes. In addition, zeolite materials have been used as adsorbents, catalyst carriers for various types of hydrocarbon conversion processes, and other applications. Zeolites are complex crystalline aluminosilicates which form a network of $AlO_2^-$ and $SiO_2$ tetrahedra linked by shared oxygen atoms. The negativity of the tetrahedra is balanced by the inclusion of cations such as alkali or alkaline earth metal ions. In the manufacture of some zeolites, non-metallic cations, such as tetramethylammonium (TMA) or tetrapropylammonium (TPA), are present during synthesis. The interstitial spaces or channels formed by the crystalline network enable zeolites to be used as molecular sieves in separation processes, as catalysts for chemical reactions, and as catalyst carriers in a wide variety of hydrocarbon conversion processes.

Zeolites include materials containing silica and optionally alumina, and materials in which the silica and alumina portions have been replaced in whole or in part with other oxides. For example, germanium oxide, tin oxide, and mixtures thereof can replace the silica portion. Boron oxide, iron oxide, gallium oxide, indium oxide, and mixtures thereof can replace the alumina portion. Unless otherwise specified, the terms "zeolite" and "zeolite material" as used herein, shall mean not only materials containing silicon atoms and, optionally, aluminum atoms in the crystalline lattice structure thereof, but also materials which contain suitable replacement atoms for such silicon and aluminum atoms.

One type of olefin-forming catalyst capable of producing large quantities of ethylene and propylene is a silicoaluminophosphate (SAPO) molecular sieve. Silicoaluminophosphate molecular sieves are generally classified as being microporous materials having 8-, 10-, or 12-membered ring structures. These ring structures can have an average pore size ranging from about 3.5 to about 15 angstroms. Preferred are the small-pore SAPO molecular sieves having an average pore size of less than about 5 angstroms, preferably an average pore size ranging from about 3.5 to about 5 angstroms, more preferably from about 3.5 to about 4.2 angstroms. These pore sizes are typical of molecular sieves having 8-membered rings.

According to one embodiment, substituted SAPOs can also be used in oxygenate-to-olefin reaction processes. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium, and lutetium; and scandium or yttrium) and the additional transition cations of Groups IVB, VB, VIIB, VIIB, VIIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a [MeO$_2$] tetrahedral unit. The [MeO$_2$] tetrahedral unit carries a net electric charge depending on the valence state of the metal substituent.

When the metal component has a valence state of +2, +3, +4, +5, or +6, the net electric charge is typically between −2 and +2. Incorporation of the metal component is typically accomplished by adding the metal component during synthesis of the molecular sieve. However, post-synthesis ion exchange can also be used. In post-synthesis exchange, the metal component will introduce cations into ion-exchange positions at an open surface of the molecular sieve, not into the framework itself.

Suitable silicoaluminophosphate molecular sieves include, but are not limited to, SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal-containing forms thereof, and mixtures thereof. Preferred SAPOs include, but are not limited to, SAPO-18, SAPO-34, SAPO-35, SAPO-44, and SAPO-47, particularly SAPO-18 and SAPO-34, including the metal-containing forms thereof, and mixtures thereof. As used herein, the term mixture is synonymous with combination and is considered a composition of matter having two or more components in varying proportions, regardless of their physical state.

An aluminophosphate (ALPO) molecular sieve can also or alternately be included in the catalyst composition. Aluminophosphate molecular sieves are crystalline microporous oxides which can have an $AlPO_4$ framework. They can have additional elements within the framework, typically have uniform pore dimensions ranging from about 3 angstroms to about 10 angstroms, and are capable of making size-selective separations of molecular species. More than two dozen structure types have been reported, including zeolite topological analogues. Preferred ALPO structures include, but are not limited to, ALPO-5, ALPO-11, ALPO-18, ALPO-31, ALPO-34, ALPO-36, ALPO-37, and ALPO-46.

The ALPOs can also include a metal substituent in their frameworks. Preferably, the metal can be selected from the group consisting of magnesium, manganese, zinc, cobalt, and mixtures thereof. These materials preferably exhibit adsorption, ion-exchange and/or catalytic properties similar to aluminosilicate, aluminophosphate, and silicoaluminophosphate molecular sieve compositions.

The metal containing ALPOs have a three-dimensional microporous crystal framework structure of $MO_2$, $AO_2$ and $PO_2$ tetrahedral units. These as-manufactured structures (which contain template prior to calcination) can be represented by empirical chemical composition, on an anhydrous basis, as:

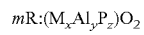

$$mR:(M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved; "x", "y", and "z" represent the mole fractions of the metal "M", (e.g., magnesium, manganese, zinc, and cobalt), aluminum, and phosphorus, respectively, present as tetrahedral oxides.

The metal-containing ALPOs are sometimes referred to by the acronym as MeAPO. Also in those cases where the metal "Me" in the composition is magnesium, the acronym MAPO is applied to the composition. Similarly ZAPO, MnAPO, and CoAPO are applied to the compositions which contain zinc, manganese, and cobalt, respectively. To identify the various structural species which make up each of the subgeneric classes MAPO, ZAPO, CoAPO, and MnAPO, each species is assigned a number and is identified, for example, as ZAPO-5, MAPO-11, CoAPO-34, and so forth.

The silicoaluminophosphate molecular sieve is typically admixed (e.g., blended) with other materials. When blended, the resulting composition is typically referred to as a SAPO catalyst, with the catalyst comprising the SAPO molecular sieve.

Materials which can be blended with the molecular sieve can be various inert or catalytically active materials, or various binder materials. These materials include compositions such as kaolin and other clays, various forms of rare earth metals, metal oxides, other non-zeolite catalyst components, zeolite catalyst components, alumina or alumina sol, titania, zirconia, magnesia, thoria, beryllia, quartz, silica, or silica sol, and mixtures thereof. These components are also effective in reducing, inter alia, overall catalyst cost, acting as a thermal sink to assist in heat shielding the catalyst during regeneration, densifying the catalyst and increasing catalyst strength. It is particularly desirable that the inert materials that are used in the catalyst to act as a thermal sink have a heat capacity of from about 0.05 to about 1 cal/g-° C., more preferably from about 0.1 to about 0.8 cal/g-° C., most preferably from about 0.1 to about 0.5 cal/g-° C.

Additional molecular sieve materials can be included as a part of the SAPO catalyst composition or they can be used as separate molecular sieve catalysts in admixture with the SAPO catalyst if desired. Structural types of small-pore molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. Structural types of medium-pore molecular sieves that are suitable for use in this invention include MFI, MEL, MTW, EUO, MTT, HEU, FER, AFO, AEL, TON, and substituted forms thereof. Specific examples molecular sieves that can be combined with a silicoaluminophosphate catalyst include ZSM-5, ZSM-34, erionite, and chabazite.

Another type of olefin-forming catalyst capable of producing large quantities of ethylene and propylene is an aluminosilicate molecular sieve. Still another type of olefin-forming catalyst capable of producing large quantities of ethylene and propylene is a non-SAPO zeolite molecular sieve. These other types of molecular sieves may not only be used in combination with SAPO molecular sieves, but indeed may be used as a complete or partial replacement for the SAPO molecular sieves described herein.

The catalyst composition, according to an embodiment, preferably comprises from about 1% to about 99%, more preferably from about 5% to about 90%, and most preferably from about 10% to about 80%, by weight of molecular sieve. It is also preferred that the catalyst composition have a particle size of from about 20 microns to about 3,000 microns, more preferably from about 30 microns to about 200 microns, most preferably from about 50 microns to about 150 microns.

The catalyst can be subjected to a variety of treatments to achieve the desired physical and chemical characteristics. Such treatments include, but are not necessarily limited to hydrothermal treatment, calcination, acid treatment, base treatment, milling, ball milling, grinding, spray drying, and combinations thereof.

A molecular sieve catalyst particularly useful in making ethylene and propylene is a catalyst which contains a combination of SAPO-34, and SAPO-18 or ALPO-18 molecular sieve. In a particular embodiment, the molecular sieve is a crystalline intergrowth of SAPO-34, and SAPO-18 or ALPO-18.

To convert oxygenate to olefin, any variety of reactor systems can be used, including fixed bed, fluid bed, or moving bed systems. Preferred reactors of one embodiment are co-current riser reactors and short contact time, countercurrent free-fall reactors. The reactor is preferably one in which an oxygenate feedstock can be contacted with a molecular sieve catalyst at a weight hourly space velocity (WHSV) of at least about 1 $hr^{-1}$, preferably in the range of from about 1 $hr^{-1}$ to 1000 $hr^{-1}$, more preferably in the range of from about 20 $hr^{-1}$ to about 1000 $hr^{-1}$, and most preferably in the range of from about 30 $hr^{-1}$ to about 500 $hr^{-1}$. WHSV is defined herein as the weight of oxygenate, and reactive hydrocarbon which may optionally be in the feed, per hour per weight of the molecular sieve in the reactor. Because the catalyst or the feedstock may contain other materials that act as inerts or diluents, the WHSV is calculated on the weight basis of the oxygenate feed, and any reactive hydrocarbon which may be present with the oxygenate feed, and the molecular sieve contained in the reactor.

Preferably, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

The process can generally be carried out at a wide range of temperatures. An effective operating temperature range can be from about 200° C. to about 700° C., preferably from about 300° C. to about 600° C., more preferably from about 350° C. to about 550° C. At the lower end of the temperature range, the formation of the desired olefin products may become markedly slow with a relatively high content of oxygenated olefin byproducts being found in the olefin product. However, the selectivity to ethylene and propylene at reduced temperatures may be increased. At the upper end of the temperature range, the process may not form an optimum amount of ethylene and propylene product, but the conversion of oxygenate feed will generally be high.

Operating pressure also may vary over a wide range, including autogenous pressures. Effective pressures include, but are not necessarily limited to, a total pressure of at least 1 psia (7 kPaa), preferably at least about 5 psia (34 kPaa). The process is particularly effective at higher total pressures, including a total pressure of at least about 20 psia (138 kPaa). Preferably, the total pressure is at least about 25 psia (172 kPaa), more preferably at least about 30 psia (207 kPaa). For practical design purposes it is desirable to use methanol as the primary oxygenate feed component and to operate the reactor at a pressure of not greater than about 500 psia (3445 kPaa), preferably not greater than about 400 psia (2756 kPaa), most preferably not greater than about 300 psia (2067 kPaa).

Undesirable byproducts can be avoided by operating at an appropriate gas superficial velocity. As the gas superficial velocity increases, the conversion decreases, avoiding undesirable byproducts. As used herein, the term, "gas superficial velocity" is defined as the combined volumetric flow rate of vaporized feedstock, which includes diluent when present in the feedstock, as well as conversion products, divided by the cross-sectional area of the reaction zone. Because the oxygenate is converted to a product having significant quantities of ethylene and propylene while flowing through the reaction zone, the gas superficial velocity may vary at different locations within the reaction zone. The degree of variation depends on the total number of moles of gas present, the cross-section of a particular location in the reaction zone, the temperature, the pressure, and other relevant reaction parameters.

In one embodiment, the gas superficial velocity is maintained at a rate of greater than 1 meter per second (m/s) at least one point in the reaction zone. In another embodiment, it is desirable that the gas superficial velocity is greater than about 2 m/s at least one point in the reaction zone. More desirably, the gas superficial velocity is greater than about 2.5 m/s at least one point in the reaction zone. Even more desirably, the gas superficial velocity is greater than about 4 m/s at least one point in the reaction zone. Most desirably, the gas superficial velocity is greater than about 8 m/s at least one point in the reaction zone.

According to yet another embodiment of the invention, the gas superficial velocity is maintained relatively constant in the reaction zone such that the gas superficial velocity is maintained at a rate greater than 1 m/s at all points in the reaction zone. It is also desirable that the gas superficial velocity be greater than about 2 m/s at all points in the reaction zone. More desirably, the gas superficial velocity is greater than about 2.5 m/s at all points in the reaction zone. Even more desirably, the gas superficial velocity is greater than about 4 m/s at all points in the reaction zone. Most desirably, the gas superficial velocity is greater than about 8 m/s at all points in the reaction zone.

The amount of ethylene and propylene produced in the oxygenate-to-olefin process can be increased by reducing the conversion of the oxygenates in the oxygenate-to-olefins reaction. However, reducing the conversion of feed oxygenates in the oxygenate conversion reaction tends to increase the amount of oxygenated hydrocarbons, particularly including dimethyl ether, that are present in the olefin product. Thus, control of the conversion of feed in the oxygenate reaction process can be important.

According to one embodiment, the conversion of the primary oxygenate, e.g., methanol, is from 90 wt % to 98 wt %. According to another embodiment the conversion of methanol is from 92 wt % to 98 wt %, preferably from 94 wt % to 98 wt %.

According to another embodiment, the conversion of methanol is above 98 wt % to less than 100 wt %. According to another embodiment, the conversion of methanol is from 98.1 wt % to less than 100 wt %; preferably from 98.2 wt % to 99.8 wt %. According to another embodiment, the conversion of methanol is from 98.2 wt % to less than 99.5 wt %; preferably from 98.2 wt % to 99 wt %.

In this invention, weight percent conversion is calculated on a water-free basis unless otherwise specified. Weight percent conversion on a water-free basis is calculated as: 100× (weight oxygenate fed on a water-free basis−weight oxygenated hydrocarbon in the product on a water-free basis)÷ (weight oxygenate fed on a water free basis). The water-free basis of oxygenate is calculated by subtracting out the water portion of the oxygenate in the feed and product and excluding water formed in the product. For example, the weight flow rate of methanol on an oxygenate-free basis is calculated by multiplying the weight flow rate of methanol by 14/32 to remove the water component of the methanol. As another example, the rate flow rate of dimethyl ether on an oxygenate-free basis is calculated by multiplying the weight flow rate of diemethyl ether by 40/46 to remove the water component of the dimethyl ether. If there is a mixture of oxygenates in the feed or product, trace oxygenates are not included. When methanol and/or dimethyl ether are used as the feed, only methanol and dimethyl ether are used to calculate conversion on a water-free basis.

In this invention, selectivity is also calculated on a water-free basis unless otherwise specified. Selectivity is calculated as: 100×wt % component/(100−wt % water−wt % methanol−wt % dimethyl ether) when methanol and/or dimethyl ether are used as the feed.

The greater the amount of dimethyl ether in the olefin product of an oxygenate-to-olefin reaction, the lower the percent conversion. Since it is desirable to run the reaction at lower conversion in order to increase selectivity to ethylene and propylene, it is desirable to have some quantity of dimethyl ether in the olefin produced. However, the amount of dimethyl ether present should not be so high as to make the overall process inefficient or the removal of dimethyl ether more difficult.

In a less than complete reaction process, dimethyl ether is typically produced. In general, the dimethyl ether will be present in the olefin produced in an oxygenate-to-olefin reaction process in an amount of at least about 100 wppm on a water-free basis. Preferably, the dimethyl ether is present in an amount of at least about 500 wppm, and more preferably at least about 1000 wppm. Preferably, the amount of dimethyl ether in the olefin stream from the oxygenate-to-olefin reaction process, on a water-free basis, is not greater than about 20 wt %, more preferably not greater than about 15 wt %, and most preferably not greater than about 10 wt %, based on total weight of the olefin stream emerging from the reactor of the oxygenate-to-olefin reaction system.

The oxygenate-to-olefin process forms a substantial amount of water as a byproduct. Much of this water byproduct is removed prior to separation of the propane and dimethyl ether-containing stream by cooling the olefin stream from the reactor to a temperature below the condensation temperature of the water vapor in the olefin stream. Preferably, the temperature of the olefin product stream is cooled to a temperature below the condensation temperature of the oxygenate feed. In certain embodiments, it is desirable to cool the product stream below the condensation temperature of methanol.

It is desirable to cool the olefin stream from the oxygenate-to-olefin reaction process, then separate the cooled olefin stream into a condensed, water-containing stream and an olefin vapor stream. The condensed, water-containing stream comprises most of the water from the olefin stream, and a significant portion of the oxygenated hydrocarbons from the olefin stream. The olefin vapor stream comprises a majority of the olefins, e.g., ethylene and propylene.

In one aspect of the invention, the olefin stream from the oxygenate-to-olefin reaction process is cooled so that a vapor stream, rich in olefins, can be separated from the condensed water-containing stream. It is desirable that the vapor stream contain not greater than about 20 wt % water, preferably not greater than about 15 wt % water, more preferably not greater than about 12 wt % water.

A quench column is one type of equipment that is effective in cooling the olefin stream from the olefin-to-oxygenate reaction process. In a quench column, a quenching fluid is directly contacted with the olefin stream to cool the stream to the desired condensation temperature. Condensation produces the condensed water-containing stream, which is also referred to as a heavy bottoms stream. The olefin portion of the olefin product stream remains a vapor and exits the quench column as an overhead vapor stream. The overhead vapor stream is rich in olefin product and can also contain some oxygenated hydrocarbon byproducts, as well as water.

In one embodiment, the quenching fluid is a recycle stream of the condensed water-containing, heavy bottoms stream of the quench column. This water-containing stream is desirably cooled, e.g., by a heat exchanger, and injected back into the quench column. It is preferred in this embodiment to not inject cooling medium from an outside source into the quench column, although it may be desirable to do so in other separation equipment downstream of the quench column.

III. Separating a Propane/DME-Containing Stream

According to the invention, a stream containing propane and dimethyl ether (referred to as a propane/DME-containing stream) can be separated from the olefin product stream formed in the oxygenate-to-olefin reaction. A portion of the propane and/or DME in the propane/DME-containing stream can be removed to form a recycle stream, and the recycle stream is combined with oxygenate feed to the oxygenate-to-olefin reactor. The DME in the recycle stream can be converted to olefin product, while the remaining propane in the recycle stream passes through the reaction system, largely unaffected. Additional propane can be generated as a byproduct in the reaction system, however.

In one embodiment of the invention, the olefin product stream containing the dimethyl ether and propane can be dried before the propane/DME-containing stream is separated out. In this embodiment, a solid or liquid drying system can be used to remove water from the olefin stream containing the dimethyl ether (i.e., dry the olefin stream) prior to distillation to more effectively remove the dimethyl ether.

In the solid drying system, the olefin stream can be contacted with a solid adsorbent to further remove water to very low levels. Any variety of methods can be used. Typically, the adsorption process can be carried out in one or more fixed beds containing a suitable solid adsorbent.

Adsorption can be useful for removing low concentrations of water, as well as for removing certain oxygenated hydrocarbons (e.g., oxygenated hydrocarbons other than DME) that may not normally be removed by using other treatment systems. Preferably, an adsorbent system used as part of this invention has multiple adsorbent beds. Multiple beds can allow for continuous separation without the need for shutting down the process to regenerate the solid adsorbent. For example, in a three-bed system, typically one bed is on-line, one bed is regenerated off-line, and a third bed is on standby.

The specific adsorbent solid or solids used in the adsorbent beds can depend on the types of contaminants being removed. Examples of solid adsorbents for removing water and various polar organic compounds, such as oxygenated hydrocarbons (e.g., oxygenated hydrocarbons other than DME) and absorbent liquids, include, but are not limited to, aluminas, silica, molecular sieves, and aluminosilicates. Beds containing mixtures of these sieves or multiple beds having different adsorbent solids can be effectively used to remove water to very low levels.

The adsorbent beds can be operated at ambient temperature or at elevated temperature as required and with either upward or downward flow. Regeneration of the adsorbent materials can be carried out by conventional methods including treatment with a stream of a dry inert gas such as nitrogen at elevated temperature.

In the liquid drying system, a water absorbent can be used to remove water from the olefin stream containing the dimethyl ether. The water absorbent can be any liquid effective in removing water from an olefin stream. The amount of water absorbent to be used is typically an amount effective in substantially reducing clathrate and free-water formation during the distillation process.

It is preferred that water absorbent be added to a water absorption vessel at a molar ratio of water absorbent to total feed entering the absorption vessel of about 1:1 to about 1:5,000, more preferably from about 1:10 to about 1:1,000, and most preferably from about 1:25 to about 1:500.

Water absorbents that can be used in this invention are liquids at 1 atm. These absorbents also desirably have an average boiling point of at least 100° F. (38° C.), preferably at least 120° F. (49° C.), and more preferably at least 150° F. (66° C.). Average boiling point, as defined herein, takes into account the boiling point of each compound in the absorbent on a weight-average basis. For example, an absorbent containing 90 wt. % of a compound having a boiling point of 100° F. (38° C.) and 10 wt. % of a compound having a boiling point of 200° F. (93° C.) would have an average boiling point of 110° F. (43° C.).

The water absorbents are also desirably polar hydrocarbon compositions. Such compositions preferably contain compounds such as monohydric alcohols, polyhydric alcohols, amines, or mixtures thereof. Preferred monohydric alcohols include methanol, ethanol, and propanol. Preferred polyhydric alcohols include glycols. Preferred glycols include ethylene glycol and tri-ethylene glycol. It is desirable that the absorbent composition contain at least about 75 wt % liquid water absorbent. The remainder of the composition can be a diluent as long as the diluent does not adversely impact water absorption. Preferably, the water absorbent composition contains at least about 85 wt % of a water absorbing compound; more preferably at least about 90 wt %, and most preferably at least about 95 wt %. Alcohols such as methanol are most preferred as the water absorbent.

Conventional absorption systems can be used in this invention to contact absorbent with olefin. In one embodiment, the absorption system uses packed columns, although plate absorption columns may also be used. In another embodiment, the absorption column has a liquid inlet located at a top portion of the absorption column. The absorbent liquid is evenly distributed across the top of the column. Desirably, an even distribution of the absorbent liquid is accomplished by using a distributor plate or spray nozzles. At the bottom of the absorption column is a gas inlet where the olefin, containing water and dimethyl ether, enters the absorption column. The vapor components move up the column countercurrent to the liquid absorbent moving down the column. This process is known as countercurrent absorption.

The packing or plates in the column can provide a surface for intimate contact between the vapor and liquid components within the column. In a countercurrent absorption column, the concentrations of soluble gases in both the liquid and vapor phases are typically greatest at the bottom of the column, and typically lowest at the top of the column. The outlet for the liquid absorbent can be at the bottom of the absorption column, typically below the gas inlet. The outlet for the gas phase lean in the gases most soluble in the liquid absorbent can be at the top of the absorption column, typically above the liquid inlet.

One or more absorption columns can be used in series or in parallel to decrease the concentration of water to desired levels and to handle larger volumes of olefin composition from the oxygenate-to-olefin process. Following absorption, the olefin stream can be distilled to remove a propane and dimethyl ether stream.

Absorbent liquid can be regenerated by conventional means. In one embodiment, the absorbent liquid containing the absorbed gases can be fed into a distillation column, and water can be removed as an overhead product. Regenerated absorbent liquid can be removed as a bottoms product.

In another embodiment of the invention, the quenched and/or dried olefin stream can be further processed by compression, preferably multi-staged compression. Two, three, four, or more stages can be used, with two or three stages being preferred.

Desirably, the quenched and/or dried olefin stream is compressed to a pressure that is greater than that at which the oxygenate-to-olefin reaction process is carried out. Preferably, the olefin stream is compressed to a pressure of at least about 30 psia (207 kPaa), more preferably at least about 50 psia (345 kPaa), most preferably at least about 100 psia (689 kPaa). High pressure ranges are particularly preferred, with the upper limit being a practical one based on cost of design and ease of operation. Practical high pressure limits are generally considered to be up to about 5,000 psia (34.5 MPaa), with lower limits of about 1,000 psia (6.9 MPaa), about 750 psia (5.2 MPaa), and about 500 psia (3.45 MPaa) being increasingly preferred.

In a preferred embodiment of the invention, the separation of the propane/DME-containing stream from the olefin product stream takes place in a distillation type of column. In one embodiment of this invention, it can be desirable to conduct distillation at a temperature range which will allow for fractionation of the olefin feedstream between the boiling point of propylene and propane. Separating the propane out in this manner will result in one stream containing the propylene and another stream containing the propane plus the dimethyl ether contained in the olefin product stream. In one embodiment, the propylene stream can be substantially polymer-grade feed quality, containing not greater than about 10 wppm dimethyl ether, for example not greater than about 5 wppm dimethyl ether, or not greater than about 1 wppm dimethyl ether.

In another embodiment of this invention, it can be desirable to conduct distillation at a temperature range which will allow for fractionation of the olefin feedstream between the boiling point of propane and dimethyl ether. Separating the propane out in this manner will result in one stream containing propane and the propylene and another stream containing the dimethyl ether contained in the olefin product stream. In this embodiment, the propylene stream can be substantially chemical-grade, typically not polymer-grade, feed quality, also containing not greater than about 10 wppm dimethyl ether, for example not greater than about 5 wppm dimethyl ether, or not greater than about 1 wppm dimethyl ether. Further in this embodiment, the propane content in the propylene- and propane-containing stream can be as high as the content of the excess propane in the system.

In a preferred embodiment of this invention, the olefin product stream containing the propane and dimethyl ether is distilled so as to separate out a propane/DME-containing stream from the other components of the olefin stream. Preferably, the olefin stream containing the propane and dimethyl ether is distilled so as to separate a propane/DME-containing stream from the olefin stream that contains from about 0.1 wt % to about 50 wt % propane, for example from about 0.1 wt % to about 15 wt % propane, from about 0.1 wt % to about 10 wt % propane, from about 20 wt % to about 50 wt % propane, or from about 25 wt % to about 45 wt % propane, based on total weight of the propane/DME-containing stream. The propane/DME-containing stream can also contain dimethyl ether in an amount of from about 50 wt % to about 99.9 wt %, for example from about 50 wt % to about 90 wt %, from about 70 wt % to about 90 wt %, or from about 50 wt % to about 70 wt %, based on total weight of the propane/DME-containing stream.

In another embodiment of the invention, a propylene stream can be recovered following distillation. The propylene stream can advantageously be substantially free of dimethyl ether, substantially free meaning having a dimethyl ether concentration so low as not to substantially adversely affect downstream processing of propylene. Preferably, the separated propylene stream can contain not greater than about 25 wppm, preferably not greater than about 10 wppm, for example not greater than about 1 wppm, or not greater than about 0.5 wppm dimethyl ether.

In another embodiment, at least about 75 wt % of the dimethyl ether in the olefin product stream containing the dimethyl ether can be separated out in the distillation process to form the propane/DME-containing stream. Alternately, at least about 85 wt %, for example at least about 90 wt % or at least about 95 wt %, of the dimethyl ether in the olefin stream can be separated out in distillation.

IV. Recycle Stream

A portion of the propane and/or DME in the propane/DME-containing stream can be removed from that stream to form the recycle stream. The amount of propane/DME removed should correspond to at least the amount of propane/DME formed in the reactor of the oxygenate-to-olefins conversion process. This propane/DME can be removed in any of a variety of ways. One example is by purging or removing a portion of the propane/DME-containing stream to form the recycle stream. The amount of the propane/DME-containing stream that is purged should include the amount of propane that was formed in the reactor of the oxygenate-to-olefins conversion process (i.e., excess amount). If the excess amount is not removed, there is a very high likelihood that the propane level will continue to rise in the reaction system, thereby causing an undue quantity of propane to be present in the reactor. Other examples of removing the excess propane include simple distillation of a portion of the propane from the propane/DME-containing stream, and absorption or adsorption of a portion of the propane and/or DME from the propane/DME-containing stream.

The recycle stream that is formed or recovered from the propane/DME-containing stream preferably contains a significant quantity of dimethyl ether such that the recycle stream can contribute as feed when added to the oxygenate stream. Preferably, at least a majority (i.e., more than 50 wt %) of the recycle stream is dimethyl ether, based on total weight of the recycle stream. More preferably, at least 60 wt %, for example at least 70 wt % or at least 80 wt % of the recycle stream can be dimethyl ether, based on total weight of the recycle stream.

In one embodiment, the recycle stream contains from 0.5 wt % to 50 wt % propane, typically from 0.8 wt % to 20 wt %, for example from 1 wt % to 10 wt % propane, based on total weight of the recycle stream.

In another embodiment, the recycle stream contains from 50 wt % to 99 wt % dimethyl ether, for example from 70 wt % to 99 wt % or from 80 wt % to 99 wt % dimethyl ether, based on total weight of the recycle stream.

V. Propylene Stream

The propylene stream that is also separated according to this invention can be polymerized to form plastic compositions, e.g., polyolefins, particularly polypropylene and olefinic propylene copolymers. Any of a variety of processes for forming polypropylene can be used. Catalytic processes are preferred. Particularly preferred are metallocene, Ziegler/Natta, aluminum oxide, and acid catalytic systems. In general, these methods involve contacting the propylene product, optionally together with a comonomer, such as another olefin, with a polyolefin-forming catalyst at a pressure and temperature effective to form the polyolefin product.

In one embodiment of this invention, the propylene product is contacted with a metallocene catalyst, optionally together with a comonomer, such as another olefin, to form a polyolefin. Preferably, the polyolefin forming process is carried out at a temperature ranging between about 50° C. and about 320° C. The reaction can be carried out at low, medium, or high pressure, being anywhere within the range of about 1 barg (100 kpag) to about 3200 barg (320 MPag). For processes carried out in solution, an inert diluent can be used. In this type of operation, it is preferred that the pressure be at a range of from about 10 barg (1 MPag) to about 150 barg (15 MPag), and more preferably at a temperature range of from about 120° C. to about 250° C. For gas-phase processes, it is preferred that the temperature generally be within a range of about 60° C. to 120° C. and that the operating pressure be from about 5 barg (500 kpag) to about 50 barg (5 MPag).

In addition to polyolefins, numerous other olefin derivatives may be formed from the at least one olefin (e.g., ethylene, propylene, and $C_{4+}$ olefins, particularly butylene) separated according to this invention. The olefins separated according to this invention can also be used in the manufacture of such compounds as aldehydes, acids such as $C_2$-$C_{13}$ mono carboxylic acids, alcohols such as $C_2$-$C_{12}$ mono alcohols, glycols such as ethylene glycol and propylene glycol, esters made from the $C_2$-$C_{12}$ mono carboxylic acids and the $C_1$-$C_{12}$ mono alcohols, linear alpha olefins, vinyl acetate, ethylene dichloride and vinyl chloride, ethylbenzene, ethylene oxide, cumene, acrolein, allyl chloride, propylene oxide, acrylic acid, ethylene-propylene rubbers, acrylonitrile, and trimers and dimers of ethylene and propylene. The $C_{4+}$ olefins, butylenes in particular, are particularly suited for the manufacture of aldehydes, acids, alcohols, and esters made from $C_5$-$C_{13}$ mono carboxylic acids.

VI. Examples of Preferred Embodiments

FIG. 1 represents one example of the overall aspect of the invention. According to the embodiment of FIG. 1, an oxygenate such as methanol (MeOH) is sent through a line 10 and combined with a recycle stream from line 26 to form a feed stream 11 that is fed to a methanol-to-olefins reaction unit 12. The recycle stream in line 26 contains dimethyl ether and propane.

Within the reaction unit 12, the feed stream contacts an oxygenate-to-olefin catalyst. This contacts converts the oxygenate components (e.g., methanol and dimethyl ether) to olefin products such as ethylene and propylene, as well as other byproducts. This total stream is generally referred to as an olefin stream. The byproducts in the olefin stream include a variety of non-olefin compounds such as water and various alkanes such as propane. The amount of propane that is formed in the reaction process is the excess amount of propane relative to the amount of the propane in the feed stream, with substantially all, if not all, of the propane in the feed coming from the recycle stream.

In one preferred embodiment, the olefin stream is sent through a line 14 to a quench unit 16, where a substantial portion of the water is removed. Following quench, the olefin stream is sent to a separator 20. The separator 20 can be any unit or combination of units effective in separating a byproduct stream of propane ($C_3°$) and dimethyl ether (DME).

As shown in the FIG. 1, a byproduct stream of propane and dimethyl ether is separated from separation unit 20 and sent by way of line 22 to an optional second separation unit 24. The separation unit 24 can be as simple as a purge stream, which is used to remove a portion of the stream 22 and reduce the total amount of propane that is recycled by way of line 26 or the separation unit 24 can be more complex, including such components as a distillation unit. In an alternative embodiment, separation unit 24 is replaced by using a distillation column in separation unit 20 in which propane is removed as a side draw. A portion of the propane, preferably an amount at least equivalent to the excess amount produced in the reaction unit 12, is preferably removed. Once the propane is removed, this stream is sent through the line 26 and is referred to as the recycle stream.

Figure 2:
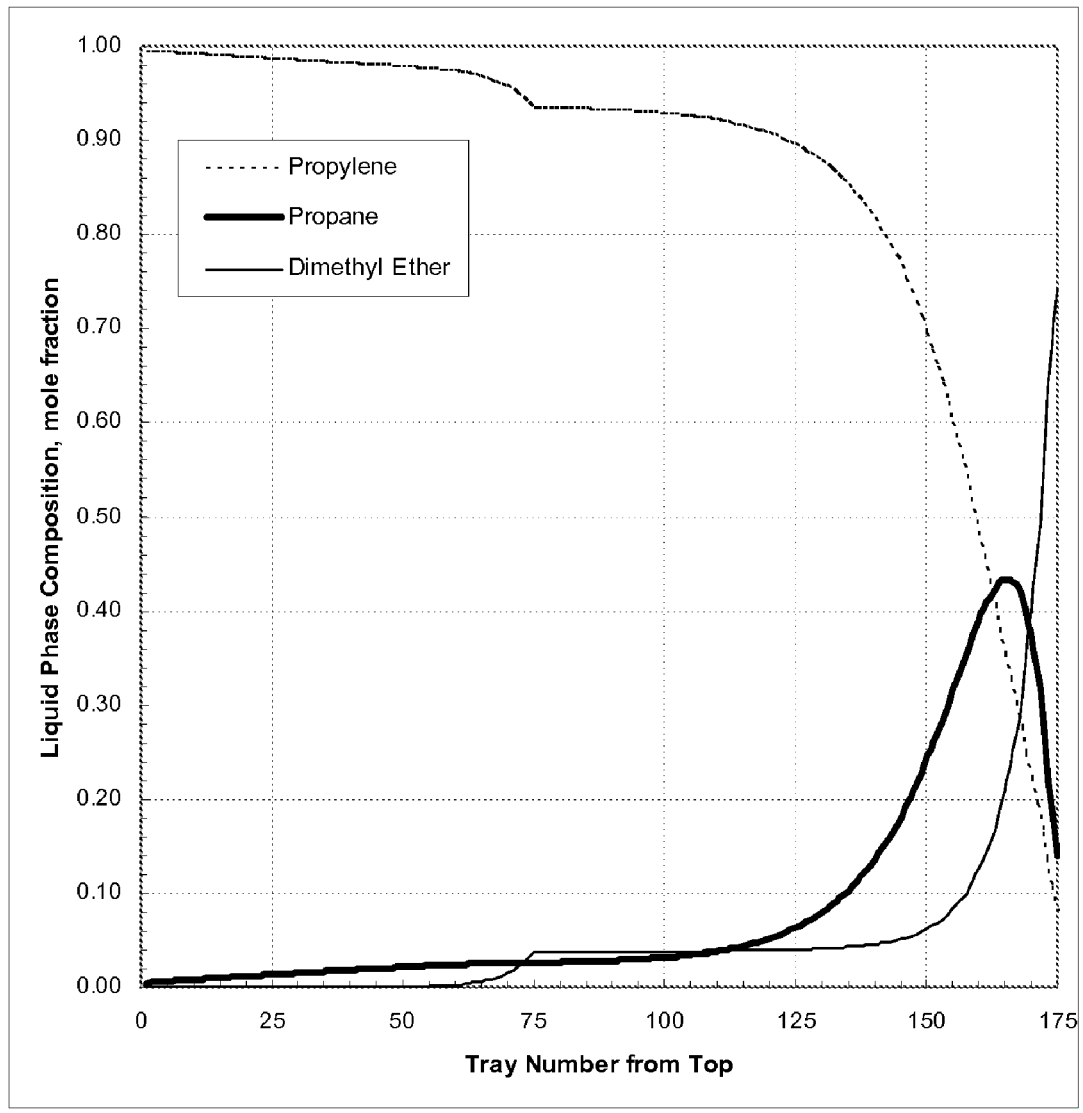
FIG. 2 is a graph of one embodiment of the invention showing a propane-rich region of a distillation column used to separate dimethyl ether and propane from propylene.

FIG. 2 shows an example of a liquid-phase composition profile for a $C_3$ splitter (i.e., distillation column) in an oxygenate-to-olefin process in which propylene is withdrawn from the top of the column and a combination of propane and dimethyl ether is withdrawn from the bottom of the column. This profile does not include any draws as a side-stream.

In the type of distillation column shown if FIG. 2, a stream containing predominantly a combination of propane, propylene and dimethyl ether is introduced as feed. FIG. 2 shows that propylene is in very high concentration at the upper end of the column, with propane and DME being in very low concentrations at the upper end. As liquid refluxes down the tower, the concentration of propylene decreases and the concentrations of propane and DME increase. The rate of increase of the concentration of propane is higher than that of DME initially. Propane concentration then reaches a maximum and begins to drop while DME concentration continues to increase. In a preferred embodiment of the invention, a draw would be taken near the location of the highest concentration of propane.

The optimal location of a side-draw to remove the propane will vary with the constitution of the feed stream, configuration of the tower (e.g., number of trays, feed tray location), and the specifications for the tower products (e.g., purity of the overhead stream and overhead recovery of propylene). In a preferred embodiment, the side-draw to remove the propane will be in a section below the midpoint of the distillation column. This section is generally referred to as the stripping section of the column. In a more preferred embodiment, the distillation column includes trays and the side-draw is taken in the bottom portion of the column, but above the reboiler. The side-draw or side-stream can be taken off as either a vapor or a liquid.

The principles and modes of operation of this invention have been described above with reference to various exemplary and preferred embodiments. As understood by those of skill in the art, the overall invention, as defined by the claims, encompasses other preferred embodiments not specifically enumerated herein.

Additionally or alternately, the invention includes a variety of embodiments, which are described below.

Embodiment 1

A process for producing one or more olefins from an oxygenate feed, comprising:
providing an oxygenate stream;
adding a recycle stream containing propane and dimethyl ether to the oxygenate stream to form a feed stream; and
contacting the feed stream with an oxygenate-to-olefin catalyst in a reactor to form an olefin stream that contains dimethyl ether, at least one olefin, and propane, wherein the propane in the olefin stream is in excess of that in the feed stream.

Embodiment 2

A process for producing olefins from an oxygenate feed, comprising:
providing an oxygenate stream;
adding a recycle stream containing propane and dimethyl ether to the oxygenate stream to form a feed stream;
contacting the feed stream with an oxygenate-to-olefin catalyst in a reactor to form an olefin stream that contains water, dimethyl ether, at least one olefin, and propane, wherein the propane in the olefin stream is in excess of that in the feed stream;

condensing water from the olefin stream to form a liquid stream and a vapor stream, wherein the vapor stream comprises at least a majority of the dimethyl ether, a majority of the at least one olefin and a majority of the propane from the olefin stream;

separating at least a majority of the propane and dimethyl ether present in the olefin stream to form a propane/DME-containing stream; and removing a portion of the propane from the propane/DME-containing stream to form the recycle stream.

Embodiment 3

A process for producing olefins from an oxygenate feed, comprising:

adding a recycle stream containing propane and dimethyl ether to an oxygenate stream to form a feed stream;

contacting the feed stream with an oxygenate-to-olefin catalyst in a reactor to form an olefin stream that contains water, dimethyl ether, at least one olefin, and propane, wherein the propane in the olefin stream is in excess of that in the feed stream;

condensing water from the olefin stream to form a liquid stream and a vapor stream, wherein the vapor stream comprises at least a majority of the dimethyl ether, a majority of the at least one olefin and a majority of the propane from the olefin stream;

separating at least a majority of the propane and dimethyl ether present in the olefin stream to form a propane/DME-containing stream; and removing propane and/or DME from the propane/DME-containing stream in an amount that is at least equal to the excess so as to form the recycle stream.

Embodiment 4

The process of embodiment 1, wherein at least a majority of the propane and dimethyl ether is separated from the olefin stream to form a propane/DME-containing stream.

Embodiment 5

The process of embodiment 4, wherein a portion of the propane and/or DME is removed from the propane/DME-containing stream to form the recycle stream.

Embodiment 6

The process of any of embodiments 1, 2, and 5, wherein the propane and/or DME that is removed is in an amount at least equal to the excess.

Embodiment 7

The process of any of the embodiments 2-6, wherein the propane and/or DME is removed by purge, distillation, or extraction.

Embodiment 8

The process of any of embodiments 2-7, wherein the propane and/or DME is removed by distillation.

Embodiment 9

The process of any of embodiments 2-8, wherein the propane and/or DME is removed as a side draw in a distillation unit.

Embodiment 10

The process of any of embodiments 2-9, wherein the propane and/or DME is removed as a side draw from a lower portion of a distillation column.

Embodiment 11

The process of any of the preceding embodiments, wherein the recycle stream contains from 0.5 wt % to 50 wt % propane, based on total weight of the recycle stream.

Embodiment 12

The process of any of the preceding embodiments, wherein the recycle stream contains from 50 wt % to 99 wt % dimethyl ether, based on total weight of the recycle stream.

Embodiment 13

A process for producing a polyolefin product comprising:
providing an olefin feed from an oxygenate feed according to the process of any of the previous embodiments; and
contacting the olefin feed, optionally along with one or more comonomers, with a polymerization catalyst under conditions sufficient to form a polymer product.

What is claimed is:

1. A process for producing one or more olefins from an oxygenate feed, comprising:
providing an oxygenate stream;
adding a recycle stream with a controlled amount of propane and dimethyl ether to the oxygenate stream to form a feed stream in order to maintain a relatively high selectivity for light olefins, wherein the recycle stream contains from 50 wt % to 99 wt % dimethyl ether, based on total weight of the recycle stream, and wherein the recycle stream contains from 0.5 wt % to 50 wt % propane, based on total weight of the recycle stream;
contacting the feed stream with an oxygenate-to-olefin catalyst in a reactor to form an olefin stream that contains dimethyl ether, at least one olefin, and propane, wherein the propane in the olefin stream is in excess of that in the feed stream;
separating at least a majority of the propane and dimethyl ether from the olefin stream to form a propane/DME-containing stream; and
separating propane from the propane/DME-containing stream in an amount that is at least as much as the amount produced in the reactor during the reaction process, thus forming the recycle stream.

2. The process of claim 1, wherein the propane and/or DME that is removed is in an amount at least equal to the excess.

3. The process of claim 2, wherein the propane and/or DME is removed by purge or distillation.

4. The process of claim 2, wherein the propane and/or DME is removed by distillation.

5. The process of claim 4, wherein the propane and/or DME is removed as a side draw in a distillation unit.

6. The process of claim 4, wherein the propane and/or DME is removed as a side draw from a lower portion of a distillation column.

7. A process for producing olefins from an oxygenate feed, comprising:
providing an oxygenate stream;
adding a recycle stream with a controlled amount of propane and dimethyl ether to the oxygenate stream to form a feed stream in order to maintain a relatively high selectivity for light olefins, wherein the recycle stream contains from 50 wt % to 99 wt % dimethyl ether, based on total weight of the recycle stream, and wherein the recycle stream contains from 0.5 wt % to 50 wt % propane, based on total weight of the recycle stream;

contacting the feed stream with an oxygenate-to-olefin catalyst in a reactor to form an olefin stream that contains water, dimethyl ether, at least one olefin, and propane, wherein the propane in the olefin stream is in excess of that in the feed stream;

condensing water from the olefin stream to form a liquid stream and a vapor stream, wherein the vapor stream comprises at least a majority of the dimethyl ether, a majority of the at least one olefin and a majority of the propane from the olefin stream;

separating at least a majority of the propane and dimethyl ether present in the olefin stream to form a propane/DME-containing stream; and separating a portion of the propane from the propane/DME-containing stream to form the recycle stream, wherein the propane is removed by distillation from the recycle stream in an amount that is at least as much as the amount produced in the reactor during the reaction process, the propane being removed as a side draw in a distillation unit.

8. The process of claim 7, wherein the propane and/or DME is removed as a side draw from a lower portion of a distillation column.

9. A process for producing olefins from an oxygenate feed, comprising:

adding a recycle stream with a controlled amount of propane and dimethyl ether to an oxygenate stream to form a feed stream in order to maintain a relatively high selectivity for light olefins, wherein the recycle stream contains from 50 wt % to 99 wt % dimethyl ether, based on total weight of the recycle stream, and wherein the recycle stream contains from 0.5 wt % to 50 wt % propane, based on total weight of the recycle stream;

contacting the feed stream with an oxygenate-to-olefin catalyst in a reactor to form an olefin stream that contains water, dimethyl ether, at least one olefin, and propane, wherein the propane in the olefin stream is in excess of that in the feed stream;

condensing water from the olefin stream to form a liquid stream and a vapor stream, wherein the vapor stream comprises at least a majority of the dimethyl ether, a majority of the at least one olefin and a majority of the propane from the olefin stream;

quenching the olefin stream to remove water, then separating at least a majority of the propane and dimethyl ether present in the olefin stream to form a propane/DME-containing stream; and removing propane and/or DME from the propane/DME-containing stream in an amount that is at least equal to the excess so as to form the recycle stream, wherein the propane and/or DME is removed by distillation, the propane being removed as a side draw from a lower portion of a distillation column, and wherein the distillation column includes trays and the side-draw is taken in the bottom portion of the column, but above the reboiler, to withdraw a stream for recycle.

10. The process of claim 1, wherein the olefin stream that contains dimethyl ether, at least one olefin, and propane, is compressed to a pressure that is greater than that at which the oxygenate-to-olefin reaction process is carried out.

11. The process of claim 10, wherein the olefin stream that contains dimethyl ether, at least one olefin, and propane is compressed to a pressure of at least about 30 psia (207 kPaa) to about 750 psia (5.2 MPaa).

12. The process of claim 10, wherein the olefin stream that contains dimethyl ether, at least one olefin, and propane is compressed to a pressure of at least about 100 psia (689 kPaa) to about 500 psia (3.45 MPaa).

13. The process of claim 7, wherein the olefin stream that contains dimethyl ether, at least one olefin, and propane, is compressed to a pressure that is greater than that at which the oxygenate-to-olefin reaction process is carried out.

14. The process of claim 13, wherein olefin stream that contains dimethyl ether, at least one olefin, and propane is compressed to a pressure of at least about 30 psia (207 kPaa) to about 750 psia (5.2 MPaa).

15. The process of claim 13, wherein the olefin stream that contains dimethyl ether, at least one olefin, and propane is compressed to a pressure of at least about 100 psia (689 kPaa) to about 500 psia (3.45 MPaa).

16. The process of claim 1, wherein the olefin stream that contains dimethyl ether, at least one olefin, and propane is dried to remove water.

17. The process of claim 7, wherein the olefin stream that contains dimethyl ether, at least one olefin, and propane is dried to remove water.

* * * * *